United States Patent

Sauter et al.

[11] Patent Number: 5,123,919
[45] Date of Patent: Jun. 23, 1992

[54] COMBINED PROSTHETIC AORTIC HEART VALVE AND VASCULAR GRAFT

[75] Inventors: Joseph A. Sauter; Louis A. Campbell, both of Austin, Tex.

[73] Assignee: Carbomedics, Inc., Austin, Tex.

[21] Appl. No.: 795,497

[22] Filed: Nov. 21, 1991

[51] Int. Cl.⁵ ............................................. A61F 2/24
[52] U.S. Cl. .............................................. 623/2; 623/1
[58] Field of Search ............................. 623/1, 2, 16, 66

[56] References Cited

U.S. PATENT DOCUMENTS

| Re. 31,040 | 9/1982 | Possis | 623/2 |
| 2,912,999 | 11/1959 | Kersh | 623/2 |
| 3,312,237 | 4/1967 | Mon et al. | 623/2 |
| 4,118,806 | 10/1978 | Porier et al. | 623/2 |
| 4,233,690 | 11/1980 | Akins | 623/2 |
| 4,781,716 | 11/1988 | Richelsoph | 623/2 |
| 4,935,030 | 6/1990 | Alonso | 623/2 |
| 5,035,709 | 7/1991 | Wieting et al. | 623/2 |
| 5,071,431 | 12/1991 | Sauter et al. | 623/2 |

Primary Examiner—David Isabella
Assistant Examiner—Gina Gualtieri
Attorney, Agent, or Firm—John R. Merkling

[57] ABSTRACT

A combined mechanical heart valve and vascular graft having a shortened transition area between the valve and the graft. The mechanical valve comprises a rigid circular annulus supporting internal leaflets. A stiffening ring surrounds the annulus and provides support for a sewing ring to attach the valve to the heart. The stiffening ring also captures a proximal end of the vascular graft between the stiffening ring and the annulus.

17 Claims, 2 Drawing Sheets

COMBINED PROSTHETIC AORTIC HEART VALVE AND VASCULAR GRAFT

BACKGROUND OF OUR INVENTION

Our invention relates to prosthetic heart valves, and in particular to prosthetic heart valves which are combined with an integral vascular graft for use in replacing a diseased aortic valve and a portion of the aorta of a patient.

Prosthetic heart valves replace diseased valves in a human heart. These valves fall generally into two categories. Biologic valves are comprised of a stent supporting three circumferential leaflets made of a flexible material. If the material is biologic in nature, it may be either a xenograft, that is, harvested from a non-human cadaver, or an allograft, that is, harvested from a human cadaver. Non-biologic material such as polyurethane might also be used.

The second major category of prosthetic heart valves is mechanical valves. These valves usually comprise a rigid annulus supporting one, two or three rigid leaflets. The annulus and leaflets are frequently formed in pyrolitic carbon, a particularly hard and wear resistant form of carbon. The annulus is captured within a sewing ring so that the valve may be attached to heart tissue at the location of the replaced valve.

Functioning valves are critical to the proper action of the heart. If a valve becomes diseased, it may be replaced by a prosthetic valve. If degeneration of a valve has occurred, however, it is likely that surrounding blood vessels are also diseased. Particularly in the case of the aortic valve, surgeons have found that not only the valve but also the adjacent aorta degenerate. Consequently, both valve and a segment of the ascending aorta may be replaced at the same time. In 1968 Bentall and DeBono described a method for attaching a commercially available graft to a Starr-Edwards mechanical heart valve for the complete replacement of an aneurysmal aorta and aortic valve. See, "A Technique for Complete Replacement of the Ascending Aorta", *Thorax,* 1968; V. 23, pgs. 338–339. After implanting the mechanical heart valve, a surgeon would stitch a segment of vascular graft to the sewing ring of the mechanical valve. The juncture between the valve and the graft was abrupt and there was usually a sharp change of diameter to be expected between the valve and the graft.

Subsequently, Shiley Corp., in conjunction with cardiovascular surgeons, produced a composite valve and preattached graft. Between the valve and the graft, there was a relatively long, tapered fabric section. It was suggested that the taper would provide a smooth transition between the valve and the graft to reduce turbulent flow. Tapered sections of 8 to 12 millimeters have been widely used by Shiley and others offering composite valve/graft combinations.

The combined valves/grafts with the extended tapered section have been effective, but have presented certain drawbacks. The method of attaching the graft inside the sewing ring requires that the valve be generally smaller than that which a surgeon would ordinarily implant. For example, a typical tapered valve/graft combination would employ a valve with the same internal orifice area as 25 millimeter aortic mechanical valve combined with a 27 millimeter sewing ring and a 30 millimeter graft. This results in a restriction in the available flow area, with associated resistance to flow. Further, fabrication of the tapered section has usually been accomplished by means of long pleats. The coronary arteries, which supply blood to the heart, enter the aorta immediately downstream from the aortic valve. These arteries must be reattached to the graft, so that blood can be supplied to the heat. The pleats in a tapered section frequently act as an obstruction to the attachment of the ostia of the coronary arteries. Moreover, since the diameter of the tapered section is usually smaller than either the graft or the aorta that is being replaced, it may be necessary to stretch the coronary arteries, putting additional strain on these critical structures.

With the foregoing in mind, it is an objective of our invention to provide a combined mechanical heart valve and graft which has an expanded valve orifice, corresponding to the diameter of the associated graft.

It has been a further object of our invention to provide a combined heart valve and graft wherein the graft is attached to the valve with little or no transitional taper.

Another object of our invention has been to provide a combined heart valve and graft wherein the graft is immediately adjacent the valve, to provide attachment sites for the ostia of the coronary arteries.

Another object of our invention has been to produce a combined heart valve and graft wherein the graft is attached to the heart valve between the annulus of the valve and the sewing ring.

These and other objects and features of our invention will be apparent from the following description taken with reference to the accompanying drawings.

SUMMARY OF OUR INVENTION

We have invented a combined mechanical heart valve and vascular graft having a shortened transition area between the valve and the graft. The mechanical valve comprises a rigid circular annulus supporting internal leaflets. Our preferred embodiment is a bileaflet valve, but a single leaflet or trileaflet valve could also be used. A stiffening ring surrounds the annulus and provides support for a sewing ring to attach the valve to the heart. The stiffening ring also captures a proximal end of the vascular graft between the stiffening ring and the annulus.

DETAILED DESCRIPTION OF OUR PREFERRED EMBODIMENT

We will now describe our preferred embodiment, with reference to the accompanying figures. Like numerals are used to designate like parts throughout.

Figure 1:
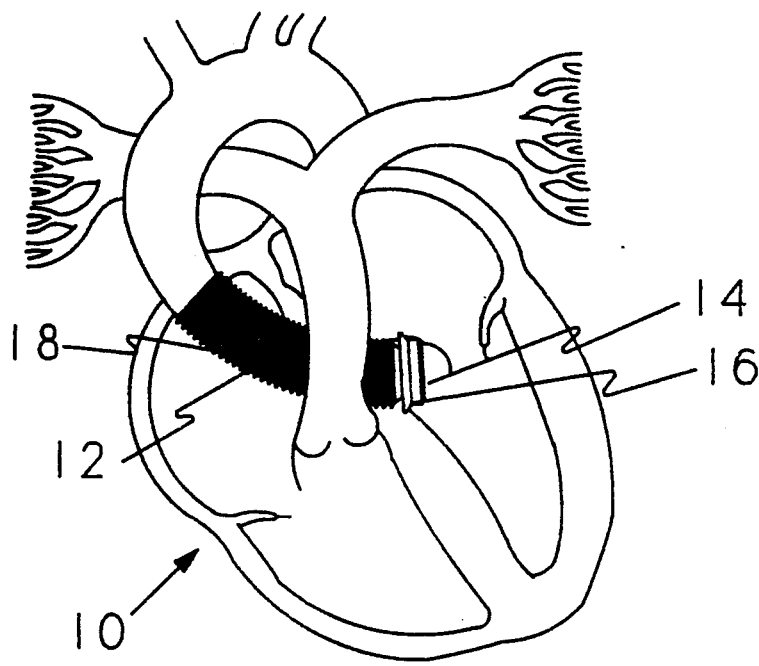
FIG. 1 is a cross-sectional view of a human heart, showing a combined mechanical heart valve and vascular graft according to our invention.

FIG. 1 illustrates a cross-sectional view of a human heart 10 with a combined mechanical heart valve and graft 12 according to our invention. The combined valve and graft 12 is shown replacing an aortic valve and a portion of the ascending aorta. The combined valve and graft comprises a mechanical heart valve 14 with a surrounding sewing ring 16. Immediately adjacent the sewing ring 16 there is a vascular graft 18. With the unique stiffening ring design, the internal diameter of the valve can be relatively large. Since the taper is very short, the ostia of the coronary arteries can be reattached to the graft 18 immediately adjacent the valve.

Figure 2:
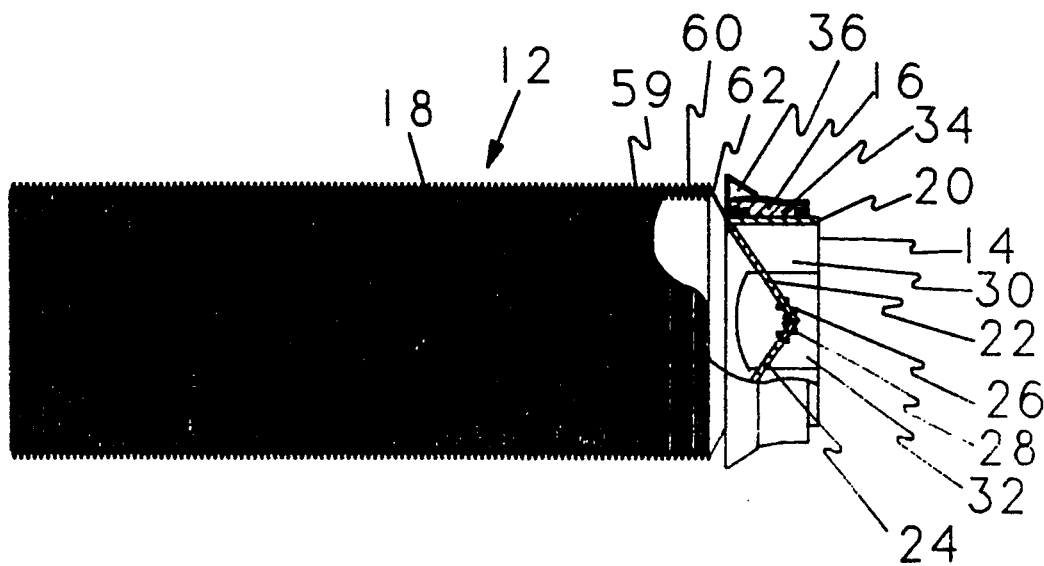
FIG. 2 is a plan view with partial cutaway section of a combined heart valve and graft according to our invention.
Figure 4:
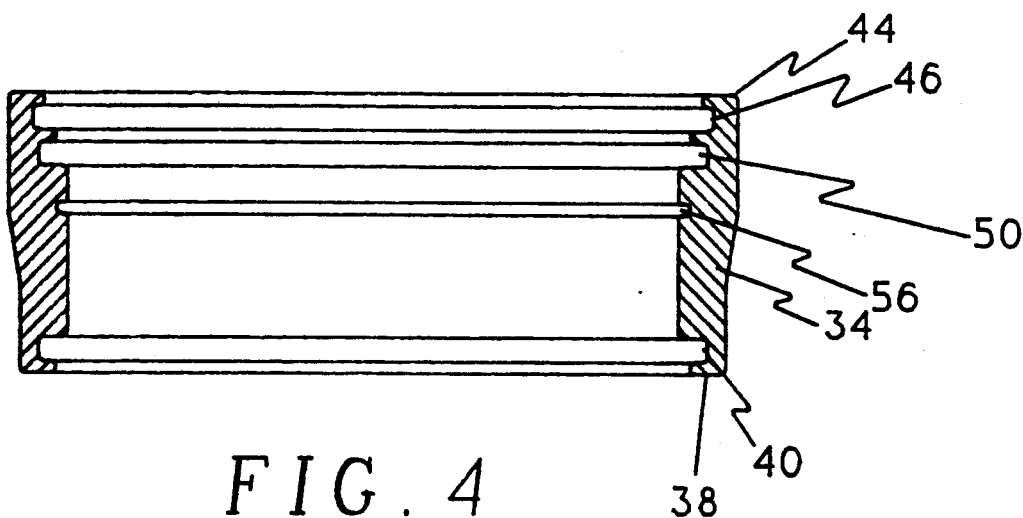
FIG. 4 is a cross-sectional plane view of a stiffening ring according to our invention.

The structure of the combined valve and graft can be more clearly seen in FIG. 2. The mechanical valve 14 comprises an annulus 20 containing leaflets 22, 24. The leaflets 22, 24 swing about pivots 26, 28. We have illustrated a bileaflet mechanical valve. In such valves, there would be two pivots for each leaflet, each pivot diametrically opposed to another across the annulus 20. Of course, a mechanical valve having one, or three, or conceivably more leaflets could also be used without departing from the spirit or teachings of our invention. On an interior side 30 of the annulus 20, adjacent the pivots 26, 28, a flattened area 32 provides a region on the annulus to support the leaflets as they pivot between open and closed positions. As is known in this art, additional conventional features may be provided, such as steps to limit the rotational motion of the leaflets.

Figure 3:
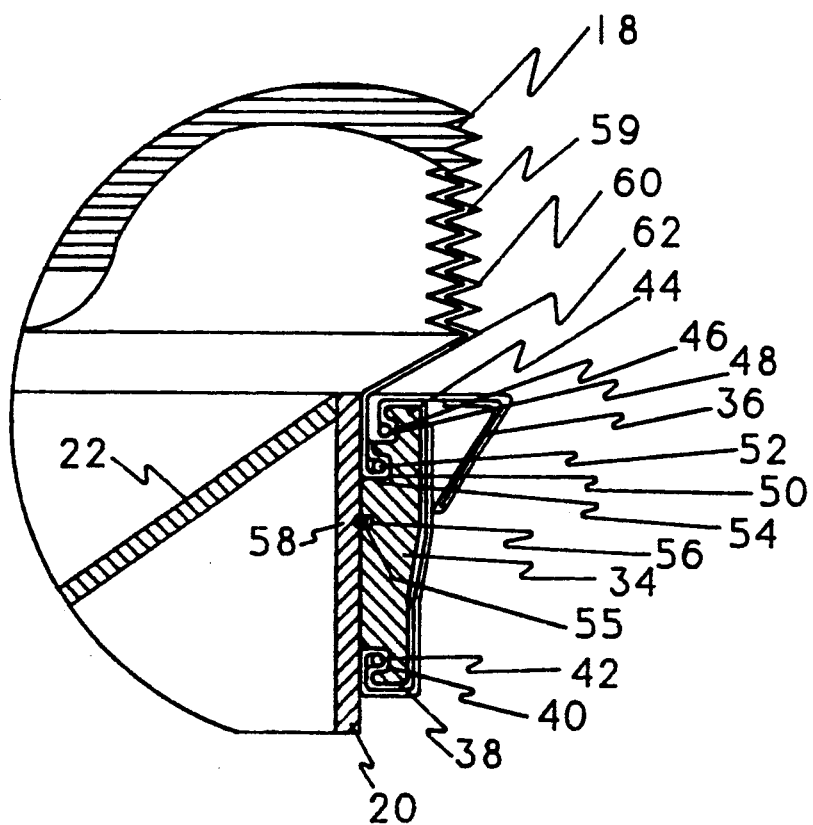
FIG. 3 is an enlarged view of a portion of the combined valve and graft of FIG. 2.

Surrounding the annulus 20, the sewing ring 16 comprises a stiffening ring 34. The annulus and leaflets are preferably formed of pyrolitic carbon which is hard and wear-resistant, but somewhat brittle. The stiffening ring 34 is usually metal, for example, colbalt-chromium or titanium alloys. A fabric sewing collar 36 is captured between the annulus 20 and the stiffening ring 34. The fabric collar 36 comprises multiple folds of cloth, as illustrated in FIG. 3. At an upstream edge 38 of the stiffening ring 34, we have made a circumferential groove 40. A fold the fabric collar 36 is captured within this groove with a metal ring 42. Similarly, at a downstream edge 44 of the stiffening ring 34, we have made a second groove 46 which captures another fold of the fabric collar 36 with a second ring 48. Immediately adjacent the downstream groove 46 we have made a third groove 50. The third groove 50 captures the vascular graft 18 between the stiffening 34 and the annulus 20, thus providing a sharp, non-stitched transition between the heart valve and the graft. A third circumferential ring 52 is placed within the third groove 50 to capture a proximal end 54 of the graft. As seen in FIG. 3, the vascular graft 18 passes between the annulus 20 and the combined stiffening ring 34 and fabric collar 36.

The annulus and leaflets are held within the sewing ring 16 by an interference ring 55 which rests in opposed grooves 56, 58 in the stiffening ring and the annulus respectively. Alternative structures for connecting an annulus and stiffening ring are shown in our U.S. Pat. No. 5,071,431, Ser. No. 07/610,084, assigned to Carbomedics, Inc.

The vascular graft 18 comprises a tubular fabric structure having corrugated walls 59. At a proximal end 60, adjacent the heart valve 14, a short taper 62 is provided. This taper is formed by taking small, stitched darts in the fabric of the graft. Usually, four darts are needed.

The tapered section 62 is extremely short and the darts do not extend into a region where the coronary arteries would be attached. To achieve the objects of our invention, the taper should measure 4 mm or less in an axial direction and preferably 2 mm or less. The ostia of the coronary arteries, therefore, can be attached into the graft 18 immediately downstream from the mechanical valve 14. Moreover, the diameter of the graft 18 at the point of attachment of the coronary arteries is relatively large. This permits the arteries to be attached without stretching.

Using experimental in-vitro models, we have found that bileaflet mechanical heart valves in test structures similar to a Sinus of Valsalva produce a large, well-established area of circular flow adjacent the walls of the Sinus of Valsalva during certain portions of a cardiac cycle. We believe this flow pattern is advantageous in a mechanical valve as it would tend to wash the areas comprising the transition between the valve and the aortic walls, diminishing the possibility of thrombosis. Our investigations have not found such a well-established flow pattern in combined heart valves and vascular grafts which have an intermediate extended taper. In the combined valve and graft of our invention, however, areas of circular flow adjacent the interface between the graft and the valve establish themselves. We believe that this will wash these areas of the combined graft and valve, thereby diminishing the possibility that thrombi may be formed.

Our invention may be embodied in other specific forms without departing from the spirit or essential characteristics thereof. Our invention therefore, is to defined by the appended claims, and not by the foregoing description. All variations which come within the meaning and doctrine of equivalency of claims, are therefore intended to be included therein.

We claim as our invention:

1. An implantable prosthetic device comprising
  a prosthetic heart valve having
    a rigid annulus,
    at least one leaflet mounted within said annulus, pivoting between open and closed positions, and
    a sewing ring surrounding said annulus, said sewing ring comprised of a stiffening ring and a fabric collar, and
  a tubular vascular graft having a proximal end and a distal end, the proximal end forming an abrupt inward taper configured to be between said annulus and said stiffening ring.

2. The implantable prosthetic device according to claim 1 wherein the stiffening ring has an upstream edge and a down stream edge, and wherein the fabric collar has an upstream part captured between said annulus and said stiffening ring near the upstream edge thereof and a downstream part captured between said annulus and said stiffening ring near the downstream edge thereof.

3. The implantable prosthetic device according to claim 2 wherein the proximal end of the vascular graft is between the annulus and both the fabric collar and the stiffening ring near the downstream edge of said ring.

4. The implantable prosthetic device according to claim 3 wherein the stiffening ring further comprises an interior wall having a first circumferential groove near the downstream edge thereof, a second circumferential groove adjacent said first groove and a third circumferential groove adjacent the upstream edge thereof, and wherein the sewing ring further comprises a first ring fitted within said first circumferential groove and retaining the downstream part of the fabric collar therein, a second ring fitted within said second circumferential groove and retaining the proximal end of the vascular graft therein, and a third ring fitted within said third circumferential groove and retaining the upstream part of the fabric collar therein.

5. The implantable prosthetic device according to claim 4 further comprising an interference ring between the annulus and the stiffening ring.

6. An implantable prosthetic device comprising
a prosthetic heart valve having
a rigid annulus,
at least one leaflet mounted within said annulus, pivoting between open and closed positions, and
a sewing ring surrounding said annulus, and
a tubular vascular graft having a proximal end and a distal end, the proximal end forming an abrupt taper connecting said annulus and said sewing ring, said taper having an axial dimension of 4 mm or less.

7. The implantable prosthetic device according to claim 6 wherein said taper is captured between said annulus and said sewing ring.

8. The implantable prosthetic device according to claim 7 wherein the sewing ring further comprises an annular stiffening ring, said stiffening ring having an upstream edge and a down stream edge, and a fabric collar, said fabric collar having an upstream part captured between said annulus and said stiffening ring near the upstream edge thereof and a downstream part captured between said annulus and said stiffening ring near the downstream edge thereof.

9. The implantable prosthetic device according to claim 8 wherein the proximal end of the vascular graft is between the annulus and both the fabric collar and the stiffening ring near the downstream edge of said ring.

10. The implantable prosthetic device according to claim 9 wherein the stiffening ring further comprises an interior wall having a first circumferential groove near the downstream edge thereof, a second circumferential groove adjacent said first groove and a third circumferential groove adjacent the upstream edge thereof, and wherein the sewing ring further comprises a first ring fitted within said first circumferential groove and retaining the downstream part of the fabric collar therein, a second ring fitted within said second circumferential groove and retaining the proximal end of the vascular graft therein, and a third ring fitted within said third circumferential groove and retaining the upstream part of the fabric collar therein.

11. The implantable prosthetic device according to claim 10 further comprising an interference ring between the annulus and the stiffening ring.

12. The implantable device according to claim 6 wherein the axial dimension of said taper is 2 mm or less.

13. The implantable prosthetic device according to claim 12 wherein said taper is captured between said annulus and said sewing ring.

14. The implantable prosthetic device according to claim 13 wherein the sewing ring further comprises an annular stiffening ring, said stiffening ring having an upstream edge and a down stream edge, and a fabric collar, said fabric collar having an upstream part captured between said annulus and said stiffening ring near the upstream edge thereof and a downstream part captured between said annulus and said stiffening ring near the downstream edge thereof.

15. The implantable prosthetic device according to claim 14 wherein the proximal end of the vascular graft is between the annulus and both the fabric collar and the stiffening ring near the downstream edge of said ring.

16. The implantable prosthetic device according to claim 15 wherein the stiffening ring further comprises an interior wall having a first circumferential groove near the downstream edge thereof, a second circumferential groove adjacent said first groove and a third circumferential groove adjacent the upstream edge thereof, and wherein the sewing ring further comprises a first ring fitted within said first circumferential groove and retaining the downstream part of the fabric collar therein, a second ring fitted within said second circumferential groove and retaining the proximal end of the vascular graft therein, and a third ring fitted within said first circumferential groove and retaining the upstream part of the fabric collar therein.

17. The implantable prosthetic device according to claim 16 further comprising an interference ring between the annulus and the stiffening ring.

* * * * *